United States Patent [19]

Tang et al.

[11] Patent Number: 5,049,682

[45] Date of Patent: Sep. 17, 1991

[54] PROCESS FOR THE PREPARATION OF HALOPHTHALIC ANHYDRIDES

[75] Inventors: David Y. Tang, Amherst; Mary K. Cocoman, Grand Island; Harry E. Buckholtz, Lewiston, all of N.Y.

[73] Assignee: Occidental Chemical Corporation, Dallas, Tex.

[21] Appl. No.: 405,606

[22] Filed: Sep. 11, 1989

[51] Int. Cl.$^5$ .................................. C07D 307/74
[52] U.S. Cl. .................................. 549/246; 549/247
[58] Field of Search .................................. 549/246, 247

[56] References Cited

U.S. PATENT DOCUMENTS 4,559,405 12/1985 Telschow .......................... 549/240
4,560,773 12/1985 Telschow .......................... 549/240

Primary Examiner—Mukund J. Shah
Assistant Examiner—Jyothsna Venkat
Attorney, Agent, or Firm—James F. Tao; Arthur S. Cookfair

[57] ABSTRACT

Halophthalic anhydrides are prepared by the liquid phase reaction of a brominating agent with halogen substituted hexa- or tetra-hydrophthalic anhydrides.

42 Claims, No Drawings

PROCESS FOR THE PREPARATION OF HALOPHTHALIC ANHYDRIDES

BACKGROUND OF THE INVENTION

This invention relates to a process for the preparation of halophthalic anhydrides by dehydrogenation of halogen substituted saturated or partially saturated phthalo compounds, such as halogen, substituted tetrahydro or hexahydro phthalic anhydrides. Halophthalic anhydrides are useful chemical intermediates for the synthesis of various commercial products, including polymers, dyes and plasticizers.

The increasing importance of high performance polyimides has led to an increased interest in halophthalic anhydrides. The latter are particularly useful as intermediates for the preparation of dianhydride monomers, such as oxydiphthalic anhydride which may be co-polymerized with a suitable diamine to form a condensation polyimide. The preparation of dianhydride monomers for the high performance polymer industry requires halophthalic anhydrides of very high purity, since the presence of even what normally would be considered as minor amounts of impurities would degrade the polymer product and perhaps render the product unsuitable for certain uses.

Halophthalic anhydrides may be prepared by the reaction of bromine with halo-substituted saturated or partially saturated phthalic anhydrides, such as halotetrahydrophthalic anhydride or gem-dihalohexahydrophthalic anhydride, at temperatures in excess of 200° Celsius. However, this approach has been found to result in relatively low yields and is in general, uneconomical.

Various other methods for the preparation of phthalic anhydrides by the dehydrogenation of saturated or partially saturated cyclic anhydrides are known in the chemical literature.

Bergmann *J. Amer. Chem. Soc.* 64, 176 (1942) discloses the aromatization of tetrahydrophthalic anhydride products of Diels-Alder reactions. The author discloses that dehydrogenation occurred when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed. Moreover, it has been found that when the dihalohexahydrophthalic anhydrides are dehydrogenated in nitrobenzene, a portion of the nitrobenzene is reduced to aniline. The aniline reacts with the anhydride group of either the starting material or product to form imides and thus lower the yield of desired product.

U.S. Pat. No. 4,560,772 to Telschow discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. Nos. 4,560,773 and 4,55,405 to Telschow disclose the preparation of substituted phthalic anhydrides by reaction of bromine with an alkyl or aryl-substituted tetrahydrophthalic anhydride, especially 4-methyltetrahydrophthalic anhydride, in the presence of an acid acceptor, such as pyridine or dimethylformamide. In the working examples, U.S. Pat. No. 4,560,773 discloses yields of 62-80% and purity of only 90-95% even after vacuum distillation. According to the patentee, the yield and purity of the desired end product would be even lower if the reaction were carried out in the absence of an acid acceptor.

U.S. Pat. No. 4,517,372 to Tang, disclose a process for the preparation of 4-fluorophthalic anhydride by dehydrogenation of gem-, difluoro- or gem-chlorofluoro- hexahydrophthalic anhydrides in the presence of a dehydrogenation catalyst, such as palladium.

U.S. Pat. No. 4,709,056 to Cotter, Lin, and Pawlak discloses the preparation of 4,4-difluorohexahydrophthalic anhydride and 4-chloro-4-fluorohexahydrophthalic anhydrides by reaction of hydrogen fluorides with 4-chlorotetrahydrophthalic anhydride.

Skvarchenko et al., Obshchei Khimii, Vol. 30, No. 11. pp. 3535–3541 disclose the aromatization of chloro-substituted tetrahydrophthalic anhydride by heating with phosphorus pentoxide. In the aromatization process described, however, decarboxylation also occurs with the formation of the corresponding chloro-substituted benzene compound. The preparation of various other tetrahydrophthalic acids and anhydrides and various methods for dehydrogenation and aromatization thereof are reviewed by Skvarchenko in Russian Chemical Review. No. 1963, pp. 571–589.

Co-pending application Ser. No. 07/393.449. which is a C-I-P of Ser. No. 160,033 and Ser. No. 160,034, is directed to the preparation of halophthalic anhydrides by the reaction of chlorine with halotetrahydrophthalic anhydride or gem-dihalohexahydrophthalic anhydride at temperatures of 200° Celsius and higher.

Although the chemical literature discloses a variety of methods for the preparation of substituted phthalic anhydrides, it will be appreciated that a need continues to exist for a more economical and efficient dehydrogenation process, suitable for the preparation of high purity halophthalic anhydrides.

SUMMARY OF THE INVENTION

It has now been found that halogen substituted phthalic anhydrides of the formula

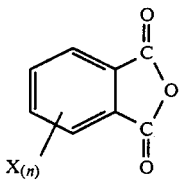

or intermediates thereof, wherein each X is independently F—, Cl—, Br—, or I—, and n is 1 or 2, may be prepared efficiently and in high yield and purity by the liquid phase reaction of a brominating agent, at temperatures below 230° Celsius, with a halogen substituted hexa-, or tetra-, hydrophthalo reactant of the formula

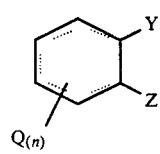

wherein Q is monohalo and is the same as X or is gem-dihalo, wherein at least one halogen is the same as X, and n is the same number as in formula I, and Y and Z are CN, COBr, COCl, or COF; or Y and Z when taken together may comprise an anhydride group. When Q is monohalo, each monohalo is directly attached to a double bond carbon and when Q is gem-dihalo, the gem-dihalo is directly attached to a non-double bond carbon. When Y and Z are CN, COBr, COCl, or COF, the product of the bromine reaction may, in a known manner, be hydrolyzed to the dicarboxylic acid which, in turn is dehydrated to form the anhydride of formula I.

DETAILED DESCRIPTION OF THE INVENTION

The starting reactants for the process of this invention, as represented by structural formula (II), above, are saturated and partially saturated halo-ortho-phthalo- hexa-, or tetra-hydroaromatic compounds including halotetrahydrophthalic anhydrides such as those of the formulae

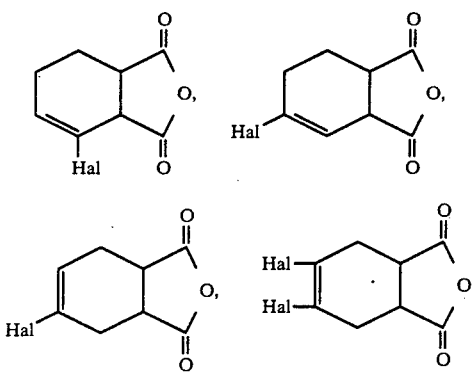

and the like, and gem-dihalohexahydrophthalic anhydrides such as those of the formula

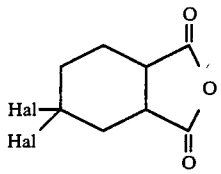

and the like, wherein Hal represents halogen; and the corresponding halotetrahydro- and gem-dihalohexahydro-ortho-phthalonitriles and ortho-phthaloyl dihalides. The preferred reactants are the saturated and partially saturated phthalic anhydrides.

The process of this invention comprises the reaction of a brominating agent with a halogen substituted cyclohexane anhydride, cyclohexene anhydride or cyclohexadiene anhydride. The preferred brominating agent, based on process efficiency and economic considerations, is elemental bromine. Other brominating agents which may be employed include, for example, N-bromosuccinimide and bromine chloride. The brominating agent is preferably employed in at least stoichiometric amounts, that is two moles of brominating agent per mole of anhydride reactant, and most preferably in an amount of up to about 10 percent excess of that stoichiometric amount. The anhydride reactant is a halogen substituted tetrahydro-ortho-phthalo compound or a gem-dihalogen substituted hexahydro-ortho-phthalo- compound. Suitable reactants are available commercially or can be prepared by various known methods. For example, the Diels-Alder reaction of a maleic anhydride with a conjugated diene will produce an anhydride with a partially saturated six-membered ring.

Depending on the desired anhydride product, the conjugated diene and/or the maleic anhydride may be selected which contain the appropriate halogen substituents. The anhydride reactants that may be employed in the process of this invention include, for example:
4-chloro-1,2,3,6-tetrahydrophthalic anhydride;
4-fluoro-1,2,3,6-tetrahydrophthalic anhydride;
4-bromo-1,2,3,6-tetrahydrophthalic anhydride;
4-chloro-1,2,5,6-tetrahydrophthalic anhydride;
4-fluoro-1,2,5,6-tetrahydrophthalic anhydride;
4-bromo-1,2,5,6-tetrahydrophthalic anhydride;
4-chloro-1,2,3,6-tetrahytdrophthalonitrile
4-fluoro-1,2,5,6-tetrahydrophthalonitrile
4-bromo-1,2,3,6-tetrahydrophthaloyl chloride
4-chloro-1,2,3,6-tetrahydrophthaloyl chloride
4,4-difluorohexahydrophthalic anhydride;
4,4-dichlorohexahydrophthalic anhydride;
4-chloro-4-fluorohexahydrophthalic anhydride;
4,4-dibromohexahydrophthalic anhydride;
4,4-difluorohexahydrophthaloyl chloride
4-chloro-4-fluorohexahydrophthalonitrile
3-chloro-1,2,5,6-tetrahydrophthalic anhydride;
3-fluoro-1,2,5,6-tetrahydrophthalic anhydride;
3-bromo-1,2,5,6-tetrahydrophthalic anhydride;
3,3-difluorohexahydrophthalic anhydride;
3,3-dichlorohexahydrophthalic anhydride;
3,3-dibromohexahydrophthalic anhydride;
3,3-difluorohexahydrophthaloyl dichloride
4,5-dichloro-1,2,3,6-tetrahydrophthalic anhydride;
4,5-difluoro-1,2,3,6-tetrahydrophthalic anhydride;
4,5-dibromo-1,2,3,6-tetrahydrophthalic anhydride;
3,4-dichloro-1,2,5,6-tetrahydrophthalic anhydride;
3,4-difluoro-1,2,5,6-tetrahydrophthalic anhydride.
The corresponding iodo compounds may be employed, but are generally less stable and are not preferred.

When the starting reactant is a saturated or partially saturated halogen substituted ortho-phthalonitrile or phthaloyl dihalide, the reaction product may be converted to an anhydride in a known manner. Thus, when a halogen substituted tetrahydrophthalonitrile, or gem dihalohexahydrophthalonitrile, is reacted with a brominating agent, in accordance with the invention, the resulting halogen substituted phthalonitrile may be hydrolyzed, in a known manner, for example, using aqueous acid, to form the dicarboxylic acid, which is then dehydrated chemically or thermally to form the corresponding halophthalic anhydrides. In addition, the halophthalonitrile may be used as an intermediate to prepare the corresponding amides or other useful end products. Using the halogen substituted tetrahydrophthaloyl dihalide, or gem-dihalohexahydrophthaloyl dihalide in the bromination reaction, results in the formation of the corresponding halo-phthaloyl dihalide which may then be hydrolyzed in a known manner to the corresponding diacid which, in turn, may be chemically or thermally dehydrated to form the corresponding anhydride. Furthermore, the halo-phthaloyl dihalides may be employed as intermediates in the formation of various esters, by alcoholysis, or in the formation of the corresponding amides by ammonolysis.

In addition to the anhydride reactants and products set forth, the applicability of the present invention to various equivalent reactants and products is contemplated. Contemplated equivalents to the anhydride reactants and products of the invention include the corresponding dicarboxylic acids, salts such as alkali metal salts, esters such as phenyl or alkylesters, imides, diamides and the like.

The process is carried out in the liquid phase, either neat or in the presence of a solvent, at atmospheric pressure or under applied or autogenous pressure at temperatures ranging from about 0° to about 230° Celsius or slightly higher and preferably about 70° to about 170° Celsius. Lower temperatures, such as 30° C. and 40° C., can be used but they are not generally preferred due to long reaction times and/or lower yields. At temperatures substantially higher than about 230° Celsius, some degradation of the reaction or the product of reaction may appear. Moreover, when the reaction mixture is heated to temperatures in excess of about 170° C., it is important that the initial reaction with bromine occur at a temperature below about 170° C.

Solvents that may be employed are preferably substantially non-reactive to bromine as well as to the organic reactant and preferably are characterized by a boiling point greater than about 100° Celsius. Typical of the solvents that may be employed are bromobenzenes and chlorobenzenes. The most preferred solvent is monochlorobenzene. Lower boiling solvents, such as chloroform, carbon tetrachloride, or chlorinated ethanes may be advantageously employed when the process is carried out at lower temperatures, for example, in the presence of a free radical initiator.

The process of the invention involves a free radical reaction which may be enhanced by the use of a free radical initiator such as visible or ultra-violet irradiation, or addition of catalytic amounts, typically less than about 5 percent by weight, based on weight of reactants, of initiators such as azo compounds, peroxides and the like. Typical azo compounds useful as free-radical initiators are azobis (alpha, gamma-dimethyl valeronitrile), 2,2'-azobis (2,4-dimethyl valeronitrile); and typical peroxides are benzoyl peroxide, diacetyl peroxide, diisopropyl peroxydicarbonate, lauroyl peroxide and the like. Azobisisobutyronitrile is particularly useful in the process of this invention. When the process is carried out in the presence of a free radical initiator, lower temperatures, typically in the range of about 0° to about 100° Celsius, may be employed.

When the process of the invention is carried out to substantial completion at a single temperature, or temperature range, it is preferred, based on yield and purity achieved, to carry it out at about 90° to 135° and preferably about 90° to 125° C. However, it has been found advantageous to carry out the reaction in at least two temperature stages, by adding the bromine reactant at temperatures of about 90° to 135° Celsius, and maintaining the temperature in that range until the bromine is substantially consumed and then increasing the temperature to above about 160° to remove any remaining dissolved HBr and convert any residual intermediates to the final product. When the bromine reactant has been substantially consumed at a lower temperature, the higher final temperature may, for example, be as high as about 250° without substantial deleterious effect. However, since temperatures greater than about 190° C. offer no particular advantage, it is preferred to employ final temperatures in the range of about 150°–160° to 190° Celsius.

In a preferred embodiment of the process of this invention, the addition of bromine to the reaction mixture is carried out in stages with associated increases in temperature. Preferably a major portion of the bromine, such as 65–80 percent, is added slowly while the reaction mixture is maintained at a temperature of about 90° to 125° Celsius until the bromine is substantially consumed. The temperature is then increased to about 130° to 145° and the remaining 20–35 percent of the bromine is added slowly while the temperature is maintained until the bromine is substantially consumed. The temperature is then increased to about 160°–175° and preferably maintained thereat for a period of time, such as about 3 to 8 hours to remove any remaining dissolved HBr and convert any residual intermediates to the final product.

During the reaction it is preferred to condense the exiting vapors at a temperature sufficient to condense bromine, but allow HBr to escape (to be recovered by scrubbers for subsequent re-use).

The following specific examples are provided to further illustrate this invention and the manner in which is may be carried out. It will be understood, however, that the specific details given in the examples have been chosen for purposes of illustration and are not to be construed as a limitation on the invention. In the examples, unless otherwise indicated, all parts and percentages are by weight and all temperature are in degrees Celsius.

EXAMPLE I

A mixture of 559.5g (3.0 moles) of 4-chlorotetrahydrophthalic anhydride and 84.0g of monochlorobenzene was heated and maintained at 105° C. while 720.0g (4.5 moles) of bromine was added over a three hour period at which time a sample of the reaction mixture was analyzed by gas chromatography and found to contain 47% (g.c. area %) 4-chlorophthalic anhydride.

The reaction mixture was heated to 135° C. and maintained thereat for 3 hours while 240.0g (1.5 moles) of bromine was added slowly, then heated to 165°–170° C. over a 20-minute period. A sample was analyzed and found to contain 79% 4-chlorophthalic anhydride. The temperature was maintained at about 165°–170° C. while 30g (.1875 mole) bromine was added over a 35-minute period. Temperature was maintained for an additional 5 hours. Final analysis of the crude reaction mixture by gas chromatography indicated (in area %) 94.7% 4-chlorophthalic anhydride, 2.1% bromophthalic anhydride and no detectable 4-chlorotetrahydrophthalic anhydride starting material. A simple up-and-over distillation at reduced pressure afforded a product of greater than 98% purity.

EXAMPLE II

A mixture of 9.3g (0.05 mole) of 4-chlorotetrahydrophthalic anhydride and 15.0g monochlorobenzene was heated to 80° C. 17.8g (0.1 mole) N-bromosuccinimide was added in small portions over a 30-minute period. An exotherm to 118° C. was observed. The reaction mixture was sampled and gas chromatograph analysis indicated 74.6% (g.c. area percent) 4-chlorophthalic anhydride. Continued heating at 90°–100° C. for ½ hour produced 84.6% 4-chlorophthalic anhydride. An additional 4.2g (.0Z3M) N-bromosuccinimide was added over a 4½ hour period at 100°–110° C. to yield reaction product containing 91.9% 4-chlorophthalic anhydride as determined by G.C.

EXAMPLE III

A mixture of 18.65 g (0.1 mole) of 4-chlorotetrahydrophthalic anhydride and 73 g of chloroform was heated to 30° C. and sparged with dry nitrogen for 15 minutes. Vazo 64 (azodiisobutyronitrile) (0.3g) was added and ultraviolet radiation applied. (GE F15T8 BLB, 15 watt black light bulb) Bromine (32g; 0.2 mole) was added slowly over a three hour period at which time a sample of the reaction mixture was analyzed by gas chromatography and found to contain 17.2% (g.c. area percent) 4-chlorophthalic anhydride. An additional 0.8g of Vazo 64 was added and the temperature was increased to 40° C. and maintained thereat for 4 hours, at which time analysis indicated 43.1% 4-chlorophthalic anhydride. A further addition of 1g of Vazo 64 and 9g of bromine (0.056 mole) was made and temperature was maintained at 40° C. for 7 more hours. Limited solubility of the reaction mixture in the amount of chloroform and the temperatures employed resulted in solids formation and the reaction was stopped with yield of 52.2% 4-chlorophthalic anhydride.

EXAMPLE IV 37.3 g (0.2 mole) of 4-chlorotetrahydrophthalic anhydride was heated to 115° C. and maintained thereat, with stirring while 70.0 g (0.4 mole) of bromine was added, sub-surface, over a four hour period. The temperature was increased to about 125° C. and an additional 7.0 g (0.04 mole) of bromine was added over a period of about 30 minutes. The reaction temperature was increased to 165°-170° C. and maintained, with stirring for four hours at which time analysis of the reaction mixture by gas chromatography indicated (in area percent) 91.1% 4-chlorophthalic anhydride as shown in Table I below.

In view of the suggestion of the prior art that the aromatization reaction of 4-methyltetrahydrophthalic anhydride with bromine is enhanced by the presence of an acid acceptor, such as pyridine, the following comparative example was carried out.

COMPARATIVE EXAMPLE IV-A

The procedure of Example IV was repeated except that an acid acceptor, pyridine (1.6 g/0.02 mole) was added to the initial reaction mixture. Results of analysis by gas chromatography are set forth in Table I.

TABLE I

| Reaction Mixture (g) | Example IV | Example IV-A |
|---|---|---|
| 4-chlorotetrahydrophthalic anhydride | 37.3 | 37.3 |
| Pyridine | | 1.6 |
| Bromine | 77.0 | 77.0 |
| Analysis of crude Reaction Product (area %) | | |
| 4-chlorophthalic anhydride | 91.1 | 84.9 |
| 4-bromophthalic anhydride | 3.2 | 1.6 |
| Phthalic anhydride | 1.0 | 10.8 |
| Other products | 4.7 | 2.7 |

From a comparison of the data of Examples IV and IV-A, it will be seen that, despite the teachings of the prior art regarding the necessity of using an acid acceptor, such as pyridine, to improve yield and purity of product in the aromatization reaction of bromine with other substituted tetrahydrophthalic anhydrides, the present process provides excellent yields and purity of product, without an acid acceptor. In fact, surprisingly, the presence of an acid acceptor in the aromatization reaction of the present invention actually results in a substantial lowering of both yield and purity of product. The impurities generated in this type of reaction, such as phthalic anhydride, are particularly difficult to separate by usual physical separation means such as conventional distillation and require costly and tedious separation steps.

EXAMPLE V 33.2 grams of 4-chlorotetrahydrophthalic anhydride was heated to 120° Celsius and maintained thereat for 4 hours while 64.4 grams of bromine was added slowly, subsurface. The temperature was increased to 130° C. and 6.4 grams of bromine added. The temperature was then increased to 164° C. and maintained thereat for 4 hours. A sample was analyzed by gas chromatography and found to contain 84.6% (g.c. area %) of 4-chlorophthalic anhydride. An additional 6.4 grams of bromine was added and after 4 hours at 164° C., the reaction mixture contained 91.1% 4-chlorophthalic anhydride.

EXAMPLE VI

To 3-necked, round bottom flask, fitted with a thermometer, condenser and additional funnel, was added 28.0 g (0.15 mole) of 4-chlorotetrahydrophthalic anhydride and 28.0 g of chlorobenzene. The flask was heated to 80° C. and 24.65 g. (0.15mole) of BrCl was added over a period of 3 hours. The temperature was increased to 95°-100° C. over the last hour of addition. The temperature was then gradually increased to 165° C. with the concurrent distillation of chlorobenzene over 2 hours. The product mixture consisted of 60.1% 4-chlorophthalic anhydride, 8.2% starting material and 13.5% intermediate dienes (GC area %). Another 8.5 g (0.05 mole) of bromine was added at 150° C. and the temperature increased to 165° C. and maintained thereat for 5½hours. The final crude reaction mixture contained 84.5% 4-chlorophthalic anhydride.

EXAMPLE VII

To a 1-l three-necked flask, equipped with a mechanical stirrer, a condenser with a gas outlet and an equa-pressured addition funnel, is charged 241.5 g (1 mole) of 4-chloratetrahydrophthaloyl chloride and 36 g of chlorobenzene. The mixture is heated to 100°-110° C. with stirring. Bromine, 320 g (2 moles) is added dropwise into the solution in a sub-surface manner. The color dissipates quickly and an evolution of gas occurs. When approximately 240 g of bromine has been added, the pot temperature is raised to 135° C. The addition of bromine continues until completion. The pot temperature is then raised to 165°-170° C. for 2-4 fours. during this period, an additional amount of bromine, such as about 10 to 15 g, may be added to complete the conversion of 4-chlorotetrahydrophthaloyl chloride. A good yield of 4-chlorophthaloyl chloride will be obtained from the distillation of the mixture.

EXAMPLE VIII

To a 1-l three-necked flask, equipped with a mechanical stirrer, a condenser with a gas outlet and an equa-pressured addition funnel, is charged 166.5 g (1 mole) of 4-chlorotetrahydrophthalonitrile and 75 g of chlorobenzene. The mixture is heated to 100°-110° C. with stirring. Bromine, 320 g (2 moles), is added dropwise into the mixture in a sub-surface manner. The red color of bromine dissipates quickly and a gas evolution starts. After about 240 g of bromine is added, the pot temperature is heated to 135° C. The addition of bromine continues until completion. The pot temperature is then raised to 165°-170° C. for 2-4 hours. During this period an additional amount of bromine, such as about 10 to 15 g, may be added to complete the conversion of 4- chlorotetrahydro-phthalonitrile. A good yield of 4-chlorophthalonitrile can be obtained by distilling out the chlorobenzene.

EXAMPLE IX

In a conventional acidic hydrolysis, the 4-chlorophthaloyl chloride or 4-chlorophthalonitrile of Examples 7 or 8 is hydrolyzed to 4-chlorophthalic acid which, upon dehydration at over 180°-200° C., will afford a high yield of 4-chlorophthalic anhydride.

EXAMPLE X

A solution of 4,5-dichlorotetrahydrophthalic anhydride (1.0 g/0.0045 mole) in trichlorobenzene (1.0 ml) was heated to 90°-100° C. A solution of bromine (0.76 g/0.0048 mole) in trichlorobenzene (1.0 ml) was added dropwise. The first few drops immediately decolorized upon addition. Subsequently, the solution turned red. During the addition, the temperature gradually rose to 110° C. Following the addition the temperature was increased to about 170° C. and maintained thereat for about one and one-quarter hour at which time 5 drops of bromine was added and the temperature was increased and maintained at about 180° C. for an additional 45 minutes. Analysis of the final reaction product by gas chromatography indicated a 90% conversion of the 4,5-dichlorotetrahydrophthalic anhydride to 4,5-dichlorophthalic anhydride.

We claim:

1. A process for the preparation of halogen substituted phthalic anhydrides of the formula

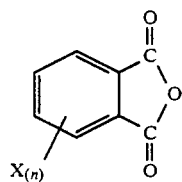

or an intermediate thereof, wherein each X is independently F—, Cl—, Br—, or I—, and n is 1 or 2, which comprises reacting in the liquid phase at temperatures below about 230° Celsius, a brominating agent, in the absence of an acid acceptor, with a halogen substituted hexa-, or tetra-hydrophthalo- reactant of the formula

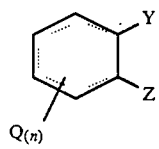

wherein Q is monohalo and is the same as X or is gem-dihalo, wherein at least one halogen is the same as X, and n is the same number as in formula I, and Y and Z are CN, COBr, COCl, or COF; or Y and Z when taken together may comprise an anhydride group, with the proviso that each monohale is directly attached to a double bond carbon and with the proviso that when Y and Z are CN, COBr, COCl, or COF, the product of the reaction with a brominating agent is hydrolyzed to the dicarboxylic acid which, in turn, is dehydrated to form the anhydride and with the proviso that when a temperature above about 170° Celsius is employed, the initial reaction will be carried out at a temperature below 170° C.

2. A process according to claim 1 wherein the temperature is below about 190° Celsius.

3. A process according to claim 1 wherein the temperature is below about 135° Celsius.

4. A process according to claim 1 wherein the temperature is below about 125° Celsius.

5. A process according to claim 2 wherein the reaction is carried out initially at a temperature below about 125° C. and the temperature is subsequently increased to below about 190° Celsius.

6. A process according to claim 5 wherein the the reaction is carried out initially at a temperature below about 125° C. and the temperature is subsequently increased to about 160° to 190° Celsius.

7. A process according to claim 2 wherein the starting material of formula II is dissolved in a solvent and the the reaction is carried out initially at a temperature below about 90° C. and the temperature is subsequently increased to a temperature below about 190° Celsius.

8. A process according to claim 2 wherein the starting material of formula II is dissolved in a solvent and the the reaction is carried out initially at a temperature below about 110° C. and the temperature is subsequently increased to a temperature of about 160° to 190° Celsius.

9. A process according to claim 1 wherein X is F, Cl, or Br.

10. A process according to claim 9 wherein Y and Z are CN.

11. A process according to claim 9 wherein Y and Z are COCl, COBr, or COF.

12. A process according to claim 11 wherein the reactant of formula II is 4-chloro-tetrahydro-orthophthaloyl dichloride.

13. A process according to claim 10 wherein the reactant of formula II is 4-chloro-tetrahydro-orthophthalonitrile.

14. A process for the preparation of halogen substituted phthalic anhydrides of the formula:

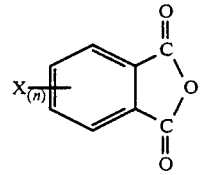

where each X is independently F—, Cl—, Br—, or I—, and n is 1 or 2, which comprises reacting a brominating agent, in the absence of an acid acceptor, with a halogen substituted hexa- or tetra- hydrophthalic anhydride reactant of the formula:

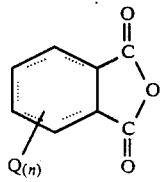

where Q is monohalo and is the same as X or is gem-dihalo, wherein at least one halogen is the same as X, and n is the same number as in formula I, with the proviso that each monohalo is directly attached to a double bond carbon and each gem-dihalo is directly attached to a non-double bond carbon, in the liquid phase at a temperature of 0° to 190° Celsius.

15. A process according to claim 14 wherein X is F—, Cl—, or Br—.

16. A process according to claim 14 carried out at a temperature of about 70° to about 170° Celsius.

17. A process according to claim 14 wherein the brominating agent is elemental bromine.

18. A process according to claim 14 wherein the brominating agent is N-bromosuccinimide.

19. A process according to claim 14 wherein the brominating agent is bromine chloride.

20. A process according to claim 14 carried out in the presence of a solvent.

21. A process according to claim 14 carried out absence of solvent.

22. A process according to claim 15 wherein the reactant of formula II is a halogen substituted tetrahydrophthalic anhydride.

23. A process according to claim 15 wherein the reactant of formula II is a gem-dihalo hexahydrophthalic anhydride.

24. A process according to claim 15 wherein the reactant of formula II is 4-chlorotetrahydrophthalic anhydride.

25. A process according to claim 22 wherein n is 1.

26. A process according to claim 22 wherein n is 2.

27. A process for the preparation of a halogen substituted phthalic anhydride of the formula:

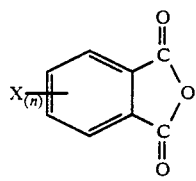

where each X is independently F—, Cl—, Br— or I—, and n is 1 or 2, which comprises reacting bromine, in the absence of an acid acceptor, at a temperature below about 230° Celsius with a halogen substituted tetrahydrophthalic anhydride reactant of the formula:

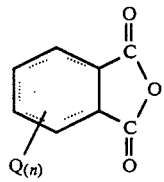

where Q is monohalo and is the same as X and n is the same number as in formula I, with the proviso that each monohalo is directly attached to a double bond carbon and with the proviso that when a temperature of about about 170° Celsius is employed, bromine is initially reacted at a temperature below 170° Celsius.

28. A process according to claim 27 wherein the temperature is below about 190° Celsius.

29. A process according to claim 28 wherein the reactant of formula II is selected from the group consisting of halotetrahydrophthalic anhydrides of the formula

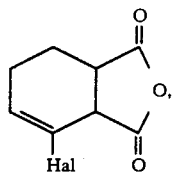 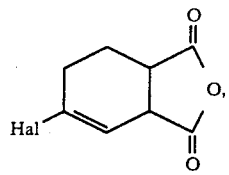

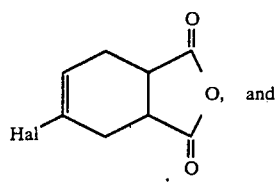 and 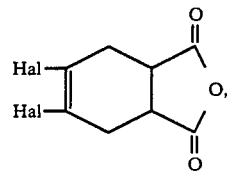

wherein Hal is F, Cl, or Br.

30. A process according to claim 29 carried out absence of solvent.

31. A process according to claim 29 carried out in the presence of a solvent.

32. A process according to claim 29 for the preparation of 4-chlorophthalic anhydride which comprises reacting bromine with 4-chlorotetrahydrophthalic anhydride.

33. A process for the preparation of a halogen substituted phthalic anhydride of the formula:

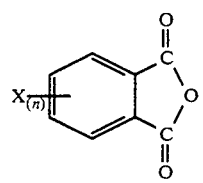

where each X is independently F—, Cl—, or Br— and n is 1 or 2, comprising the reaction of bromine, in the absence of an acid acceptor, with a halogen substituted tetrahydrophthalic anhydride reactant of the formula

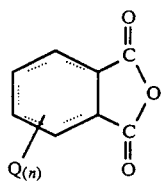

where Q is halo and is the same as X and n is the same number as in formula I, with the proviso that each halo is directly attached to a double bond carbon; wherein the reaction temperature is maintained initially at about 90° to 135° Celsius while the major portion of the bromine is added and until the bromine is substantially consumed and then increased to above about 150° Celsius.

34. A process according to claim 33 wherein the reactant of formula II is selected from the group consisting of halotetrahydrophthalic anhydrides of the formula

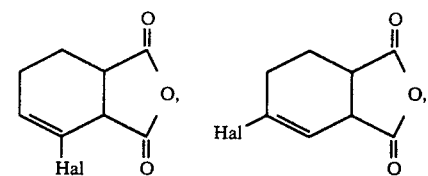

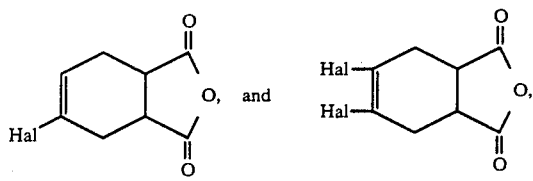

wherein Hal is F, Cl, or Br.

35. A process according to claim 34 carried out in the presence of a solvent.

36. A process according to claim 35 wherein the reactant of formula II is 4-chlorotetrahydrophthalic anhydride.

37. A process according to claim 36 wherein the solvent is monochlorobenzene.

38. A process for the preparation of a halogen substituted phthalic anhydride of the formula:

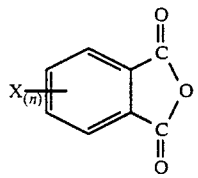

I where each X is independently F—, Cl—, or br— and n is 1 or 2, comprising the reaction of bromine, in the absence of an acid acceptor, with a halogen substituted tetrahydrophthalic anhydride reactant of the formula

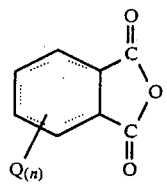

II where Q is halo and is the same as X and n is the same number as in formula I, with the proviso that each halo is directly attached to a double bond carbon; wherein the reaction comprises the steps of:

A) Adding the major portion of the bromine to a reaction mixture comprising the reactant of formula II and maintaining the reaction mixture at a temperature of about 90° to 125° Celsius until the bromine is substantially consumed;

B) Increasing the temperature to about 130° to 145° Celsius and maintaining thereat while the remaining portion of the bromine is added and substantially consumed; and C) Increasing the temperature to about 160° to 175° C.

39. A process according to claim 38 wherein the reactant of formula II is selected from the group consisting of halotetrahydrophthalic anhydrides of the formula

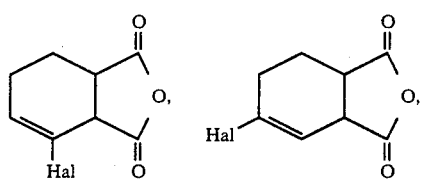

wherein Hal is F, Cl, or Br.

40. A process according to claim 39 wherein the reactant of formula II is 4-chlorotetrahydrophthalic anhydride.

41. A process according to claim 40 carried out in the presence of a solvent.

42. A process according to claim 41 wherein the solvent is monochlorobenzene.

* * * * *